United States Patent [19]

Harmon

[11] Patent Number: 5,057,087
[45] Date of Patent: Oct. 15, 1991

[54] HYPODERMIC NEEDLE SAFETY SYSTEM

[76] Inventor: James E. Harmon, 24 Margo Dr., Fairport, N.Y. 14450

[21] Appl. No.: 342,299

[22] Filed: Apr. 24, 1989

[51] Int. Cl.$^5$ .............................................. A61M 5/00
[52] U.S. Cl. .................................. 604/198; 604/192; 604/110
[58] Field of Search ............... 604/192, 198, 263, 110, 604/218, 187

[56] References Cited

U.S. PATENT DOCUMENTS

| | | | |
|---|---|---|---|
| 4,631,057 | 12/1986 | Mitchell | 604/198 |
| 4,702,738 | 10/1987 | Spencer | 604/198 |
| 4,737,144 | 4/1988 | Choksi | 604/198 |
| 4,738,663 | 4/1988 | Bogan | 604/198 |
| 4,743,233 | 5/1988 | Schneider | 604/192 |
| 4,747,837 | 5/1988 | Hauck | 604/198 |
| 4,752,290 | 6/1988 | Schramm | 604/198 |
| 4,874,383 | 10/1989 | McNaughton | 604/198 |
| 4,908,023 | 3/1990 | Yuen | 604/198 |
| 4,927,417 | 5/1990 | Moncada et al. | 604/198 |
| 4,932,940 | 6/1990 | Walker et al. | 604/110 |

FOREIGN PATENT DOCUMENTS 0350186 1/1990 European Pat. Off. ............ 604/198

Primary Examiner—John D. Yasko
Assistant Examiner—Mark O. Polutta
Attorney, Agent, or Firm—Robert J. Bird

[57] ABSTRACT

The disclosed hypodermic syringe includes a syringe barrel, a needle extending from the barrel, a movable safety sleeve surrounding the barrel, and a sleeve cap to cover the forward end of the sleeve. The syringe barrel includes a forward detent, an intermediate detent, and a rear detent, and the safety sleeve includes an inner ring for selective engagement with the detents. The safety sleeve is axially movable on the syringe barrel from an initial transport position on the intermediate detent, to a retracted position on the rear detent to expose the needle, and to a locked safety position on the forward detent. The sleeve cap is held on the safety sleeve by friction when the sleeve is in the transport position, and by positive engagement with the safety sleeve when the sleeve is in the locked safety position.

7 Claims, 2 Drawing Sheets

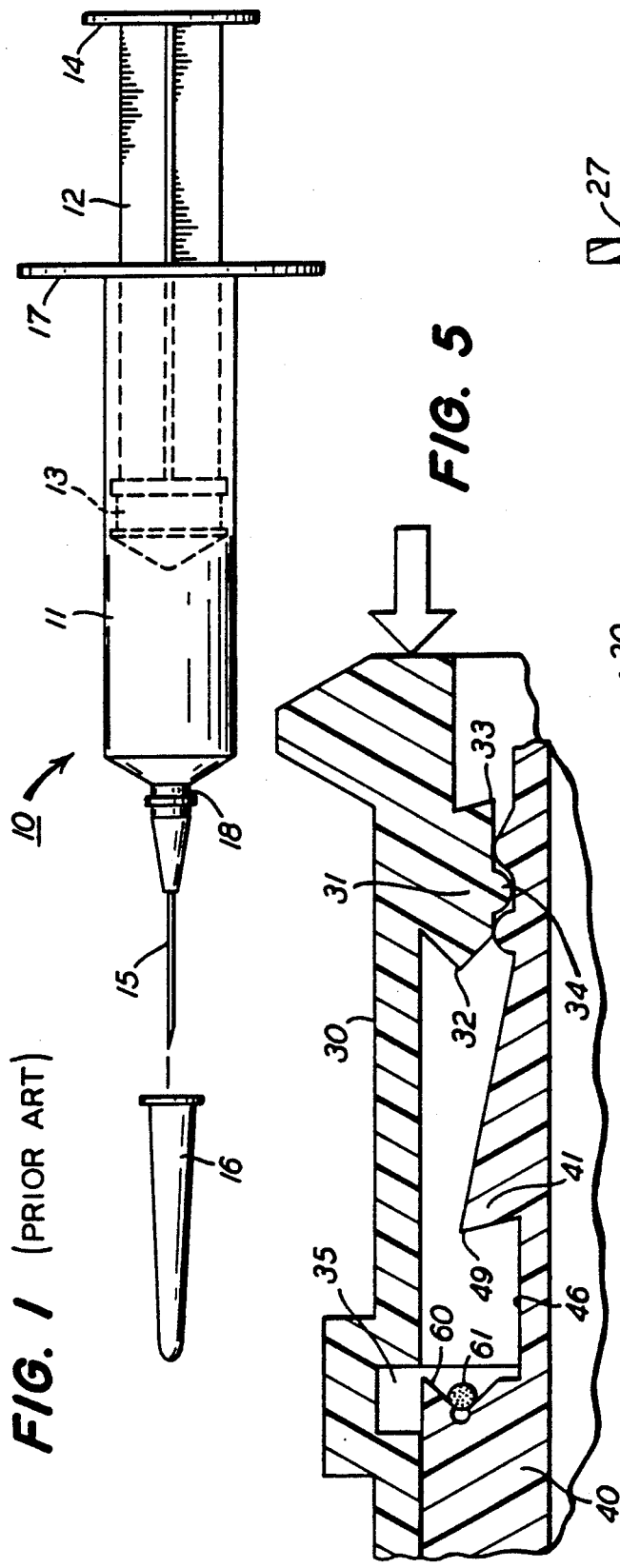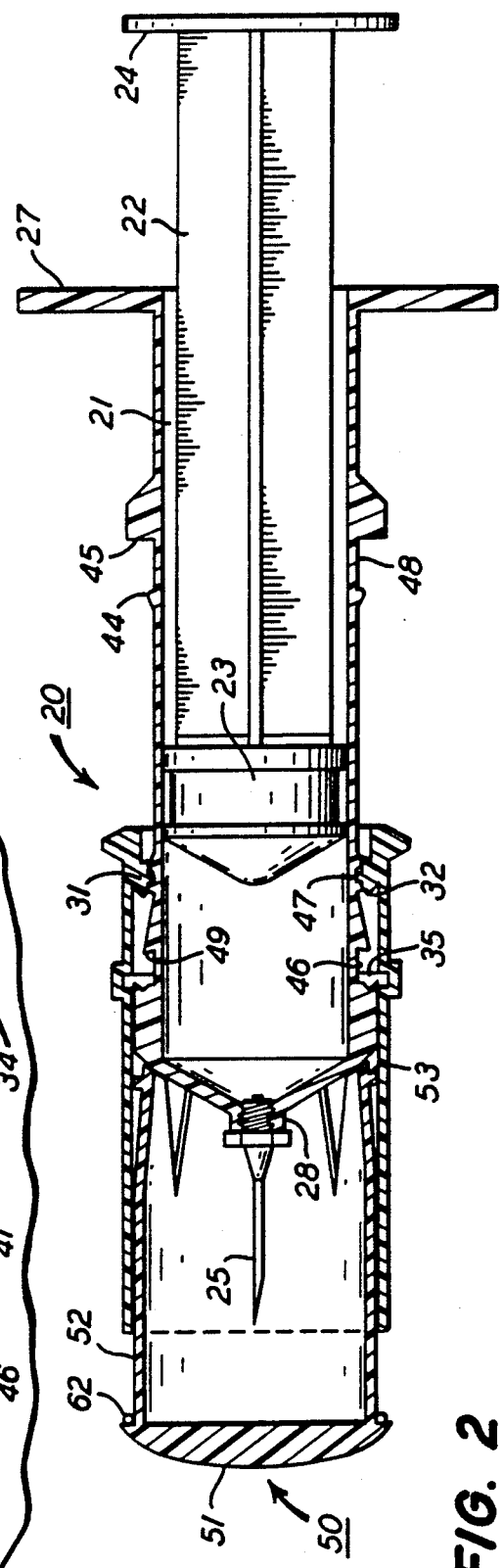

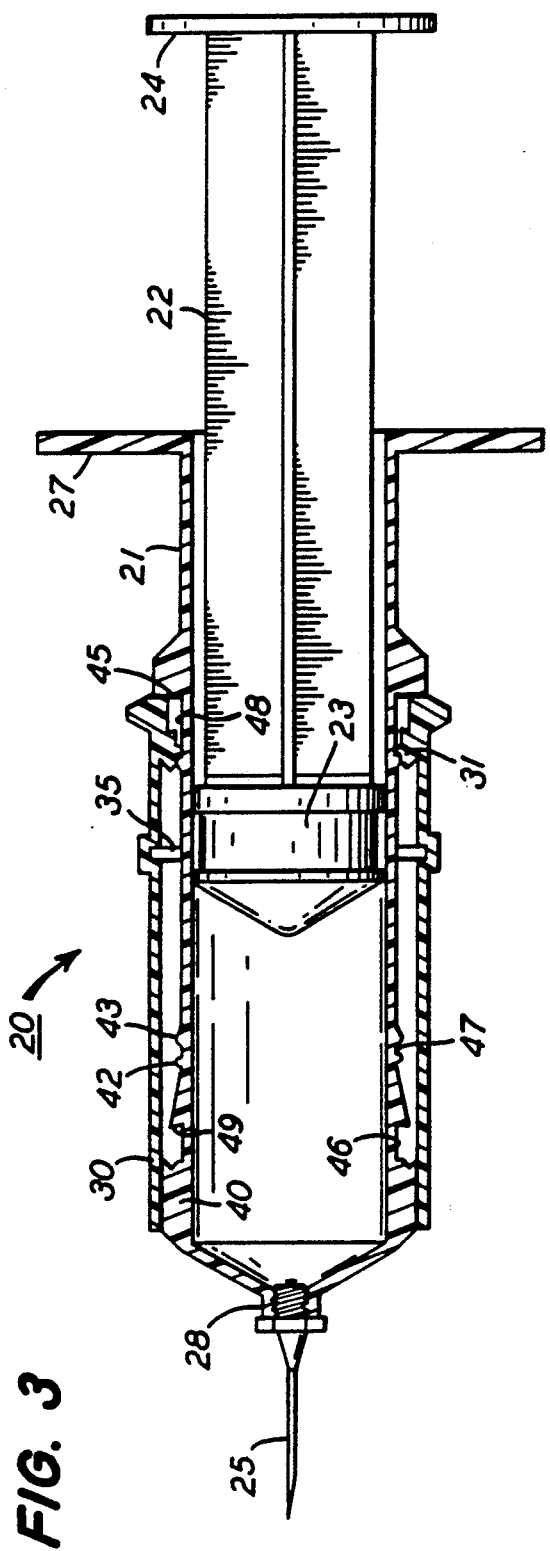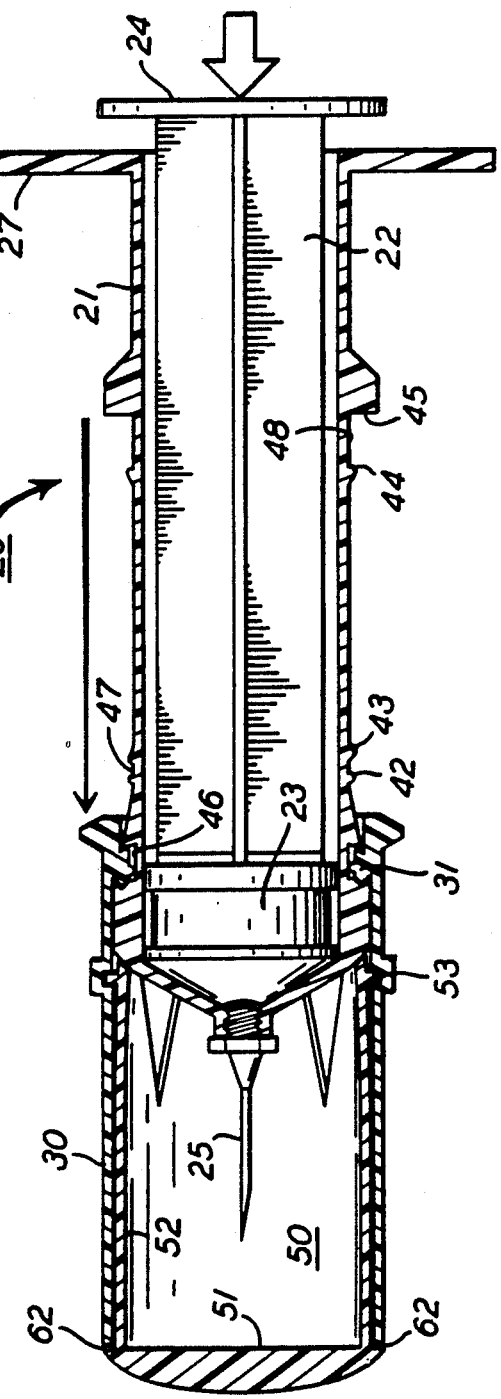

HYPODERMIC NEEDLE SAFETY SYSTEM

BACKGROUND OF THE INVENTION

1. Field of the Invention

This invention relates to hypodermic syringes and needles. More specifically, it relates to a safety system to insure against accidental pricking by a used, contaminated needle and to prevent the escape of contaminants from a used needle.

2. Background Information

The potential spread of infectious contamination from hospital and other medical refuse has always been a problem because of the possibility of infection by contact with such refuse. Today, the problem is more significant than ever because of the possibility that such refuse is contaminated with the AIDS virus against which there is no known defense. Health professionals must be very cautious with patients requiring any form of invasion of tissue for diagnostic or treatment.

Hypodermic syringes and other needle bearing devices used in hospitals and physicians' offices are an area of special concern. A used needle may be contaminated with the AIDS virus and therefore a potentially deadly instrument.

Hypodermic syringes with removable protective needle caps are known. A typical protective needle cap is an elongated thin sleeve, fit over the needle and held in place by frictional or threaded engagement with the needle hub. It is a small and separate piece, and therefore easily and frequently misplaced once it has been removed from the syringe assembly. After removing the cap and using the syringe, it is well known in the art that replacing the cap on the used syringe, if indeed the cap is not already lost, is risky. The needle must be carefully guided into the thin cap as one would sheath a sword. In rush and nerve-wracking circumstances, such as in an emergency room, one's hands may not always be steady enough to recap the used needle safely. Close proximity to others using such devices in such an environment is also a potential danger. It is also common practice to simply drop used syringes and other debris on the floor during life saving treatment in a trauma center or emergency room, creating a danger to anyone involved in the emergency and to those cleaning up or walking in the debris. These same risks exist even in normal use of these devices, until the devices are properly disposed of. Disposal is not always immediate. It is not uncommon for a nurse to carry, in a pocket, a used syringe with a loose needle cap while answering patient calls along the way to a disposal station. In short, used hypodermic needles are dangerous.

A safer hypodermic syringe is greatly to be desired to protect care-providers, waste disposal personnel, and patients from the possibility of wounds from used hypodermic syringes.

SUMMARY OF THE INVENTION

In summary, the present invention is a hypodermic syringe including a syringe barrel, a needle extending from the barrel, a movable safety sleeve surrounding the barrel, and a sleeve cap to cover the forward end of the sleeve. The syringe barrel includes a forward detent, an intermediate detent, and a rear detent, and the safety sleeve includes an inner ring for selective engagement with the detents. The safety sleeve is axially movable on the syringe barrel from an initial transport position on the intermediate detent, to a retracted position on the rear detent to expose the needle, and to a locked safety position on the forward detent. The sleeve cap is held on the safety sleeve by friction when the sleeve is in the transport position, and by positive engagement with the safety sleeve when the sleeve is in the locked safety position.

BRIEF DESCRIPTION OF THE DRAWINGS

FIG. 1 is a partial sectional view of a hypodermic syringe typical of the prior art.

FIG. 2 is a partial sectional view of a hypodermic syringe with a safety shield according to this invention. The device is shown prior to use.

FIG. 3 shows the same syringe with its safety sleeve retracted and the needle exposed for use.

FIG. 4 shows the same syringe after its use, with the safety sleeve in its locked safety position over the needle.

FIG. 5 is an enlarged sectional detail of a modified form of this invention, showing the safety sleeve moving toward its locked position.

DESCRIPTION

Referring now to FIG. 1, a hypodermic syringe 10, typical of the prior art, includes a hollow cylindrical barrel 11, a movable plunger rod 12 with a piston 13 on its forward end within the barrel and a thumb grip 14 at its rearward end external of the barrel, and a hollow hypodermic needle 15 mounted on a hub 18 on the forward end of the barrel. Barrel 11 includes finger grips 17 at its rearward end. A removable protective needle cap 16 is an elongated thin sleeve to cover the needle 15 and hub 18 before and after the needle is used. The cap 16 is held in place by frictional or threaded engagement with the hub 18. Consider the user holding the cap 16 in one hand and the syringe 10 in the other. The potential danger of pricking oneself while replacing the cap over the used needle is readily apparent.

FIGS. 2, 3, and 4 show a hypodermic needle device or syringe 20 according to this invention. The syringe 20 includes a hollow cylindrical barrel 21, a movable plunger rod 22 with a piston 23 on its forward end within the barrel and a thumb grip 24 at its rearward end external of the barrel, and a hollow hypodermic needle 25 mounted on a hub 28 on the forward end of the barrel. Barrel 21 includes finger grips 27 at its rearward end.

The exterior of the barrel 21 includes a number of spaced annular rings 40–45. The forward ring 40 is a forward stop member. Ring 40 and the next adjacent ring 41 together form a forward annular detent groove 46 between them. Rings 42 and 43 together form an intermediate annular detent groove 47 between them. Ring 44 and the rearmost ring 45 together form a rear annular detent groove 48 between them. The rearmost ring 45 is a rear stop member. Rings 42, 43 and 44 are tapered in both axial directions. Ring 41 is tapered only toward the rear and includes a barbed front edge 49. Ring 41 is also of slightly larger outside diameter than rings 42, 43 and 44.

An axially movable cylindrical safety sleeve 30 surrounds the barrel 21. Sleeve 30 includes an inwardly projecting annular ring 31 at its rearward end, and an annular groove 35 at an intermediate axial position. Ring 31 is of such shape as to include a sharp forward edge 32, a barbed rear edge 33, and an inner bead 34.

A sleeve cap 50 is adapted to fit in the forward end of the safety sleeve. Cap 50 includes a cover 51, a cylindrical side wall 52, and an annular locking ring 53 around the side wall 52 near its open end, adapted for snap locking engagement with the annular groove 35 in the safety sleeve 30.

FIG. 2 shows the syringe prior to its use, with the safety sleeve 30 in a forward needle-protective "transport" position over the needle 25. In this position, ring 31 of the sleeve 30 rests within the intermediate annular detent groove 47 on the barrel. The sleeve cap 50 is held in place on the forward end of the sleeve 30 by friction with the inner surface of the sleeve. In this new and unused state of the syringe 20, the locking ring 53 of the cap 50 and its mating annular groove 35 in the sleeve 30 are axially displaced from each other to prevent their locking engagement so that the sleeve cap 50 is removable from the sleeve 30 when the syringe is to be used.

FIG. 3 shows the syringe with its sleeve cap 50 removed and the safety sleeve 30 retracted, exposing the needle 25 for use. In this position, ring 31 of the sleeve 30 abuts the rear stop 45 on the barrel and ring 31 of the sleeve rests within the rear annular detent groove 48 to hold the sleeve 30 in this retracted position. The syringe is now ready for filling and injection.

FIG. 4 shows the syringe after its use, with the safety sleeve 30 in a forward locked safety position (as distinguished from the needle-protective "transport" position of FIG. 2) over the needle 25. The sleeve 30 has been pushed forward, its ring 31 has moved out of the rear detent groove 48, over and past the intermediate detent groove 47, into the forward detent groove 46, abutting the forward stop 40 on the barrel. Ring 31 and sleeve 30 are locked in the forward detent groove 46 by the annular ring 41 on the barrel, which prevents further retraction of the safety sleeve. The tapered ramp shapes of the annular ring 41 on the barrel and of the inward ring 31 on the sleeve facilitate their relative axial movement in one direction but not the other. The barbs 33 on the sleeve and 49 on the barrel prevent further retraction of the sleeve 30. Because of the larger outside diameter of annular ring 41, it requires greater force to lock the safety shield 30 than it does to move it to any other detent position. This is to help insure that locking must be deliberate and will not happen by accident. With the sleeve 30 now in its safety position, its annular groove 35 is accessible to the mating locking ring 53 of the cap 50 for positive engagement. The sleeve cap 50 is replaced on the forward end of the sleeve 30, and the mating ring 53 and groove 35 engage to permanently lock the cap in place.

In use, the safety sleeve is moved from its initial needle-protective "transport" position (FIG. 2) to its retracted position (FIG. 3) for filling the syringe. After filling, the sleeve is moved forward again into the transport position (FIG. 2) for transport to the patient. The sleeve is then retracted (FIG. 3) for injection, and then immediately moved forward into the locked safety position (FIG. 4).

The coaction between barrel 21 and sleeve 30 has been described as a relatively simple snap action. It is contemplated that a bayonet engagement or a threaded engagement of barrel and sleeve at the forward and rear stops might also be effectively used.

FIG. 5 is an enlarged detail of a modified form of this invention, showing the syringe with the needle sleeve 30 moving from its retracted position toward its safety position. The purpose of this configuration of the syringe is to provide a locking safety sleeve 30 which, in addition to being locked in its safety position, is also permanently sealed. The syringe of FIG. 5 is a modification of the syringe of FIGS. 2-4. The forward stop 40 includes an annular recess or groove 60 which is open in the axial direction facing the ring 31 of the safety sleeve 30. The groove 60 contains dyed glue in capsules 61 positioned in small pockets around the circumference of the groove. The forward edge 32 of the ring 31 is sharp so that it pierces the glue capsules and squeezes the glue out when the sleeve 30 is pushed into its locking position against the forward stop 40. When the glue capsules are ruptured, the glue flows by capillary action around the juncture of the ring edge 32 and the annular groove 60 of the forward stop 40 to form a seal between the barrel 21 and the sleeve 30. A fast setting low viscosity "super glue" which is fast setting (approx. 2-10 sec.) or a solvent to chemically weld the barrel-sleeve juncture is recommended. The locking action described in connection with FIGS. 2-4 occurs here also, and is effective to hold the barrel 21 and sleeve 30 together while the glue flows and sets. It is preferred to include also a brightly colored dye in the glue. This will indicate at a glance that the syringe is contaminated and locked. A similar glue sealing arrangement may also be added to the connection of cap 50 on sleeve 30, which is actuated by firm placement of the cap on the safety sleeve to seal the juncture of cap and safety sleeve, thus providing a completely sealed needle container. Alternatively, a simple O-ring 62 might also be used at the juncture of cap and sleeve.

A typical syringe of the prior art has volume scale markings on the barrel. In a syringe according to this invention, the safety sleeve may obscure such markings on the barrel. It is contemplated that scale markings might instead be put on the plunger rod.

In the use of the syringe of this invention, the user does not have to point a used needle at his own fingers and aim it into a slim sheath as has been necessary to replace the prior art needle cap. Instead, the safety sleeve is put in its safety position by a movement away from the user, locked in this position in less than one second, and the syringe then safely set aside. This device will protect the needle prior to its use, and will protect persons from the needle after its use until its destruction.

In this specification, the terms "forward" and "rearward", and variations of these terms, refer respectively to the needle end and the plunger rod end of the syringe.

It will be apparent that this invention is applicable to hypodermic devices generally. A hypodermic device of the type used to draw blood samples by vacuum means is an example.

This invention has been described in connection with a preferred embodiment thereof. Alternatives, modifications, and variations of this invention may become apparent to others skilled in the art. It is intended to embrace all such alternatives, modifications, and variations as are within the spirit and scope of the following claims.

What is claimed is:

1. A hypodermic needle device including a barrel, a needle extending forwardly from said barrel, and a safety sleeve surrounding said barrel and axially movable thereon:

said barrel including a forward detent an intermediate detent and a rear detent, and said safety sleeve adapted for selective operative engagement with said detents;

said safety sleeve being movable to selective positions on said barrel, including a transport position in engagement with said intermediate detent, a retracted position in engagement with said rear detent, and a locked safety position in engagement with said forward detent;

said safety sleeve including an inner ring tapered to permit axial movement of said ring relative to said intermediate and rear detents: and sealing means responsive to the operative engagement of said sleeve with said forward detent to form a liquid tight seal at the juncture of said sleeve and said barrel.

2. A hypodermic needle device as defined in claim 1, in which said sealing means includes a quantity of sealing liquid contained in said forward detent and responsive to impact by said sleeve to flow throughout the juncture of said sleeve and said barrel to seal said juncture.

3. A hypodermic needle device as defined in claim 2, in which said sealing liquid is dye colored to provide visible indication when said syringe is locked.

4. A hypodermic needle device including a barrel, a needle extending forwardly from said barrel, a safety sleeve surrounding said barrel and axially movable thereon, and a sleeve cap adapted to cover the forward end of said safety sleeve;

said barrel including a forward detent, an intermediate detent, and a rear detent, and said safety sleeve adapted for selective operative engagement with said detents;

said safety sleeve being movable to selective positions on said barrel, including a transport position in engagement with said intermediate detent, a retracted position in engagement with said rear detent, and a locked safety position in engagement with said forward detent;

said safety sleeve including an inner ring tapered to permit axial movement of said ring relative to said intermediate and rear detents;

said sleeve cap including an annular locking ring therearound, said ring being compressible for frictional engagement on said safety sleeve when said sleeve is in said transport position, and expandable for locking engagement on said safety sleeve when said sleeve is in said locked safety position; and sealing means responsive to the operative engagement of said sleeve with said forward detent to seal the juncture of said sleeve and said barrel.

5. A hypodermic needle device as defined in claim 4, in which said sealing means includes a quantity of sealing liquid contained in said forward detent and responsive to impact by said sleeve to flow throughout the juncture of said sleeve and said barrel to seal said juncture.

6. A hypodermic needle device as defined in claim 5, in which said sealing liquid is dye colored to provide visible indication when said syringe is locked.

7. A hypodermic needle device as defined in claim 4, further including sealing means responsive to the positive engagement of said cap with said safety sleeve to form a liquid tight seal at the juncture of said cap and said safety sleeve.

* * * * *